US008636642B2

(12) United States Patent
Dubi et al.

(10) Patent No.: US 8,636,642 B2
(45) Date of Patent: Jan. 28, 2014

(54) IN VIVO DEVICE FOR ASSISTING AND IMPROVING DIASTOLIC VENTRICULAR FUNCTION

(75) Inventors: Shay Dubi, Tel Aviv (IL); Eran Hirszowicz, Ramat-Gan (IL)

(73) Assignee: Corassist Cardiovascular Ltd., Herzliya (IL)

( * ) Notice: Subject to any disclaimer, the term of this patent is extended or adjusted under 35 U.S.C. 154(b) by 755 days.

(21) Appl. No.: 11/663,346

(22) PCT Filed: Sep. 22, 2005

(86) PCT No.: PCT/IL2005/001014
§ 371 (c)(1),
(2), (4) Date: Sep. 24, 2007

(87) PCT Pub. No.: WO2006/033107
PCT Pub. Date: Mar. 30, 2006

(65) Prior Publication Data
US 2008/0071134 A1    Mar. 20, 2008

Related U.S. Application Data

(60) Provisional application No. 60/611,711, filed on Sep. 22, 2004.

(51) Int. Cl.
*A61F 2/00* (2006.01)
*A61F 13/00* (2006.01)

(52) U.S. Cl.
USPC .............................................. 600/37; 600/16

(58) Field of Classification Search
USPC ...................................................... 600/16, 37
See application file for complete search history.

(56) References Cited

U.S. PATENT DOCUMENTS

| | | | | |
|---|---|---|---|---|
| 5,558,617 A * | 9/1996 | Heilman et al. | ................. | 600/16 |
| 5,702,343 A | 12/1997 | Alferness | | |
| 6,077,214 A * | 6/2000 | Mortier et al. | ................... | 600/16 |
| 6,702,732 B1 | 3/2004 | Lau et al. | | |
| 6,730,016 B1 * | 5/2004 | Cox et al. | ......................... | 600/37 |
| 7,124,493 B2 * | 10/2006 | Lau et al. | ......................... | 29/557 |
| 2004/0002626 A1 * | 1/2004 | Feld et al. | ....................... | 600/37 |
| 2005/0113635 A1 * | 5/2005 | Whayne et al. | .................. | 600/37 |

OTHER PUBLICATIONS

International Search Report for PCT/IL2005/001014 dated Jun. 30, 2006.
Colucci and Braunwald Heart Disease : Review and Assessment "Chapter 13: Pathophysiology of Heart Failure", third edition, 1997, Saunders Company Publishers, 12 pages.
Vasan et al., "Diastolic Heart Failure—No Time to Relax", New England Journal of Medicine 2001, vol. 344, pp. 56-59, 5 pages.

(Continued)

*Primary Examiner* — Joseph Stoklosa
(74) *Attorney, Agent, or Firm* — Nixon & Vanderhye P.C.

(57) ABSTRACT

The present invention is primarily directed towards an anatomically-compatible and physiologically-compatible in vivo device for improving diastolic function of either the left or right ventricle of the heart, wherein said device comprises at least one elastic component in the form of a lattice capable of being arranged in a curved conformation such that one surface of said lattice may be adapted to the curvature of the external ventricular surface of the heart, or a portion thereof, and wherein said at least one elastic component is capable of being operatively connected to the external ventricular surface of the heart by means of one or more connecting elements.

14 Claims, 5 Drawing Sheets

(56) References Cited

OTHER PUBLICATIONS

Opie, H. L. "The Heart Physiology, From Cell to Circulation", third edition, Lippincott-Raven publishers, 1998, chapter 12, pp. 343-389.

Mandinov et al., "Diastolic Heart Failure", Cardiovascular Research, vol. 54, Issue 4, Mar. 2000, pp. 813-825, 20 pages.

"How to Diagnose Diastolic Heart Failure", European Heart Journal, 1998, vol. 19, pp. 990-1003.

Gandhi et al., "The Pathogenesis of Acute Pulmonary Edema Associated with Hypertension," New England Journal of Medicine, 2001, vol. 344, pp. 17-22, 8 pages.

Sweitzer et al., "Diastolic Heart Failure: Miles to go Before We Sleep," American Journal of Medicine, 2000, vol. 109, pp. 683-685, 5 pages.

Grauer, "Heart Failure, Diastolic Dysfunction and the Role of the Family Physician," American Family Physician, 2001, vol. 63, pp. 1483-1486, 4 pages.

Philbin et al., "Systolic Versus Diastolic Heart Failure in Community Practice: Clinical Features, Outcomes, and the Use of Angiotensin-Converting Enzyme Inhibitors," American Journal of Medicine, 2000, vol. 109, pp. 605-613, 9 pages.

Morris-Thurgood et al., "Pacing in Heart Failure: Improved Ventricular Interaction in Diastole Rather Than Systolic Re-Synchronization," Europace, 2000, vol. 2, pp. 271-275.

Nagel et al., "Cardiac Rotation and Relaxation in Patients with Aortic Valve Stenosis", European Heart Journal, vol. 21, Apr. 2000, pp. 582-589.

Braunwald, "Heart Failure", Harrison's Principles of Internal Medicine, $4^{th}$ Edition, McGraw Hill Publishers, Chapter 233, pp. 1287-1298.

* cited by examiner

IN VIVO DEVICE FOR ASSISTING AND IMPROVING DIASTOLIC VENTRICULAR FUNCTION

This application is a U.S. continuation-in-part of international application PCT/IL2005/001014 filed 22 Sep. 2005, which designated the U.S. and claims benefit of U.S. Provisional Application Nos. 60/611,711 filed 22 Sep. 2004, the entire contents of each of which are hereby incorporated by reference.

FIELD OF THE INVENTION

The present invention relates to a device for improving ventricular function of the heart and, more particularly, to a modified in vivo device for improving diastolic function of the left ventricle of the heart.

BACKGROUND OF THE INVENTION

Heart failure is commonly defined as the inability of the left ventricle, herein, also referred to as LV, to generate an adequate cardiac output at rest or during exertion, while operating at a normal or enhanced LV filling pressure. Congestive heart failure (CHF) is a clinical syndrome in which heart failure is accompanied by the symptoms and signs of pulmonary and/or peripheral congestion. Heart failure is most commonly associated with impaired LV systolic function. A widely used index for quantifying systolic function is 'ejection fraction' (EF), defined as the ratio of stroke volume to end-diastolic volume, which can be estimated using techniques such as radiocontrast, radionuclide angiography, and/or, echocardiography. The normal value of EF is $0.67\pm0.08$, which is frequently depressed in systolic heart failure even when the stroke volume is normal. A value of $EF \geq 0.50$ is commonly used as an indicator of normal systolic function. It is notable, however, that as much as 30-50% of all patients with typical symptoms of congestive heart failure have a normal or slightly reduced ejection fraction, that is, a value of $EF \geq 0.45$.

In these patients, diastolic dysfunction is implicated as a major contributor of congestive heart failure. In some patients, systolic and diastolic heart failure coexist. The most common form of heart failure, the one caused by coronary arteriosclerosis, is an example of combined systolic and diastolic failure, as described in "Braunwald's Heart Disease: Review and Assessment", third edition, 1997, Saunders Company Publishers. There are about 4.6 million people in the United States with heart failure, and about 550,000 are being reported annually, as indicated by Vasan, R. S., and Benjamin, E. J., in "Diastolic Heart Failure—No Time to Relax", New England Journal of Medicine 2001, 344: 56-59. Also indicated therein, is that the mortality rate from diastolic heart failure (DHF), 5-12% annually, is about four times that among persons without heart failure and half that among patients with systolic heart failure, and that, nonetheless, rates of hospitalization and health care associated with diastolic heart failure rival those associated with systolic heart failure.

Primary diastolic dysfunction is typically observed in patients with hypertension and hypertrophic or restrictive cardiomyopathy, but can also occur in a variety of other clinical disorders and has a particularly high prevalence in the elderly population. Aging is associated with 'physiologic' diastolic dysfunction due to the increase in LV muscle mass and changes in passive elastic properties of the myocardium, hence, the concern of an increase in the incidence of diastolic dysfunction as the aging of the western world population progresses.

For the purpose of clearly understanding, and implementing, the following described preferred embodiments of the present invention, relevant details, description, and, definitions of selected terms, well known to one of ordinary skill in the art, of physiological and pathological aspects, mechanisms, and functions, of the heart, in general, and of the ventricles and atria, in particular, are provided herein. Additional details, description, and, definitions of terms, thereof, are readily available in the scientific literature.

The left ventricle is the chamber on the left side of the heart that receives oxygenated arterial blood from the left atrium and contracts to drive it into the aorta for distribution to the body. The right ventricle is the chamber on the right side of the heart that receives deoxygenated venous blood from the right atrium and drives it into the pulmonary artery in order to receive oxygen from the lungs. Diastole is the normal rhythmically occurring relaxation and dilatation (stretching, expansion, dilation) of the heart cavities (ventricles), during which the cavities are filled with blood. Atrial contraction occurs during the last stage of diastole of the ventricle and aids ventricular filling. Systole is the rhythmic contraction of the heart, especially of the ventricles, by which blood is driven through the aorta and pulmonary artery after each dilation or diastole.

Ventricular filling starts just after mitral valve opening. As the LV pressure decreases below that in the left atrium, the phase of rapid or early filling of the LV accounts for most of ventricular filling. LV filling temporarily stops as pressures in the atrium and left ventricle equalize, commonly known as the phase of diastasis, occurring prior to atrial contraction and during which little blood enters the filled left ventricle. Atrial contraction increases the pressure gradient from the atrium to the left ventricle to renew filling. When the LV fails to relax normally, as in 'LV hypertrophy', increased atrial contraction can enhance late filling. Relaxation (inactivation of contraction) is a dynamic process that begins at the termination of contraction and occurs during isovolumetric relaxation and early ventricular filling. 'Myocardial elasticity' is the change in muscle length for a given change in force. 'Ventricular compliance' is the change in ventricular volume for a given change in pressure, and, 'ventricular stiffness' is the inverse of compliance.

The 'preload' is the load present before contraction has started and is provided by the venous return that fills the ventricle during diastole. The 'Frank Starling law of the heart' states that the larger the volume of the heart, the greater the energy of its contraction and hence the stroke volume is larger. In other words, when the preload increases, the left ventricle distends (widens, expands) and the stroke volume increases, as described by Opie, H. L., in "The Heart Physiology, From Cell To Circulation", third edition, Lippincott-Raven publishers, 1998. The pressure-volume relation curves are an accepted description of the ventricular function.

Figure 1:
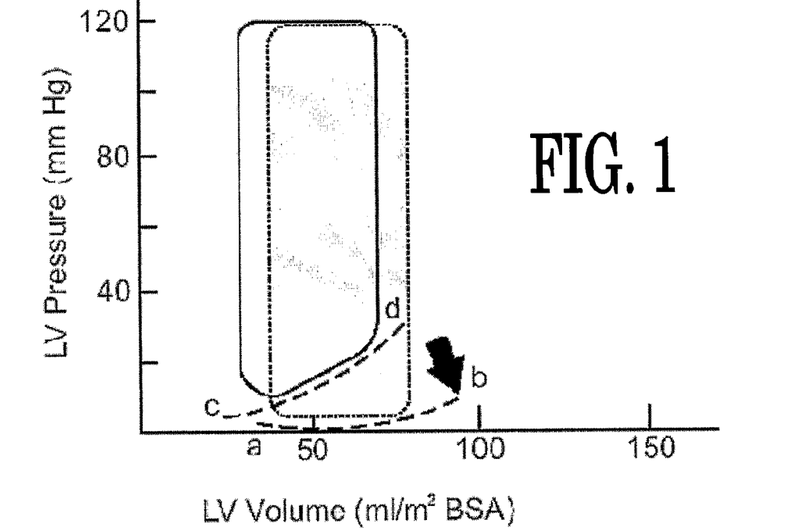
FIG. 1 is a schematic diagram illustrating a typical pressure-volume loop of a normal subject and a patient with diastolic dysfunction.

FIG. 1, adapted from the previously cited "Braunwald's Heart Disease Review and Assessment" reference, is a schematic diagram illustrating a typical pressure-volume loop of a normal subject (dotted line) and a patient with diastolic dysfunction (solid line), wherein dashed lines, between the letters "a" and 'b', and, 'c' and 'd', represent the diastolic pressure-volume relation of the normal subject, and, the patient with diastolic dysfunction, respectively. FIG. 1 shows that isolated diastolic dysfunction is characterized by a shift in the pressure-volume loop to the left. Contractile performance is normal, associated with an ejection fraction (EF) value$\geq 0.45$, with a normal or slightly decreased stroke volume. However, LV (left ventricular) pressures throughout diastole are increased, at a common diastolic volume equal to about 70 ml/m². In the patient with diastolic failure, LV end diastolic pressure is about 25 mm Hg, compared with an LV end diastolic pressure of about 5 mm Hg in the normal subject. Thus, diastolic dysfunction increases the modulus of chamber stiffness. A main objective of treating the patient with diastolic dysfunction is to cause the diastolic pressure-volume relation curve (dashed line between 'c' and 'd') to go back to the diastolic pressure-volume relation curve (dashed line between 'a' and 'b', also indicated by the arrow), of the normal subject, by decreasing the end diastolic LV pressure for the same LV volume.

The fundamental problem in diastolic heart failure (DHF) is the inability of the left ventricle to accommodate blood volume during diastole at low filling pressures, as described by Mandinov, L., Eberli, F. R., Seiler, C., and Hess, M. O., in "Diastolic Heart Failure", Cardiovascular Res. 2000, 45: 813-825. Initially, hemodynamic changes may be manifested only in an upward displacement of the diastolic pressure-volume curve in the presence of a normal end-diastolic volume with inappropriate elevation of LV diastolic, left atrial and pulmonocapillary pressure (as previously described above, with reference to FIG. 1). More severe resistance to LV filling may cause inadequate filling even in enhanced diastolic pressure with an additional leftward shift of the diastolic pressure-volume relation, resulting in a decreased end diastolic volume and depressed stroke volume, as described by Mandinov, L., et al.

Currently, four different pathophysiological mechanisms are known and used for understanding and/or explaining diastolic heart failure (DHF), combinations of which may readily take place in a particular patient: (1) slow isovolumic left ventricular relaxation, (2) slow early left ventricular filling, (3) reduced left ventricular diastolic distensibility, and, (4) increased left ventricular chamber stiffness or increased myocardial muscle stiffness, as described in the report, "How To Diagnose Diastolic Heart Failure: European Study Group On Diastolic Heart Failure", European Heart Journal, 1998, 19: 990-1003.

Slow isovolumic left ventricular relaxation, (1), refers to a longer time interval between aortic valve closure and mitral valve opening and a lower negative peak ventricular dP/dt. Regional variation in the onset, rate, and extent of myocardial lengthening is referred to as 'diastolic asynergy'; temporal dispersion of relaxation, with some fibers commencing to lengthen later than others, is referred to as 'asynchrony'. Slow early left ventricular filling, (2), is a result of slow myocardial relaxation, segmental incoordination related to coronary artery disease and the atrioventricular pressure gradient. Reduced left ventricular diastolic distensibility, (3), refers to an upward shift of the LV pressure-volume relation on the pressure-volume plot, irrespective of a simultaneous change in slope. Reduction in LV end diastolic distensibility is usually caused by extrinsic compression of the ventricles as in cardiac tamponade. Increased LV chamber stiffness or increased myocardial muscle stiffness, (4), as manifested by a shift to a steeper ventricular pressure-volume curve, is due to processes such as ventricular hypertrophy, endomyocardial fibrosis, disorders with myocardial infiltration (for example, amyloidosis) and replacement of normal, distensible myocardium with non-distensible fibrous scar tissue in healed infarct zones.

The previously cited European Study Group proposed criteria for the diagnosis of DHF. Accordingly, simultaneous presence of the following three criteria is considered obligatory for establishing a diagnosis of DHF: (1) evidence of CHF, (2) normal or mildly abnormal LV systolic function, (3) evidence of abnormal LV relaxation, filling, diastolic distensibility, or, diastolic stiffness.

Pulmonary edema is the result of the increase in pulmocapillary pressure and is due to a shift of liquid from the intravascular compartment to the lung interstitial compartment. Pulmonary edema is frequently associated with hypertension. Gandhi, S. K. et al., in "The Pathogenesis Of Acute Pulmonary Edema Associated With Hypertension", New England Journal of Medicine, 2001, 344: 17-22, have contradicted the hypothesis that pulmonary edema, apparently associated with hypertension, in patients with preserved ejection fraction, is due to transient systolic dysfunction. They found that the LV ejection fraction and the extent of regional wall motion measured during the acute episode of hypertensive pulmonary edema were similar to those measured after the resolution of the congestion, when the blood pressure was controlled, thus concluding that the pulmonary edema was due to diastolic rather than systolic heart failure.

The management of diastolic heart failure is difficult. There have been no large-scale, randomized controlled trials of therapy in diastolic heart failure, and there remains substantial disagreement about the appropriate therapy for this disease, according to Sweitzer, N. K., and Stevenson, L. W., in "Diastolic heart Failure: Miles To Go Before We Sleep", American Journal of Medicine, 2000, 109: 683-685. Medical therapy of diastolic dysfunction is often empirical and lacks clear-cut pathophysiologic concepts, as indicated in previously cited Mandinov, L. et al. No single drug presently exists which selectively enhances myocardial relaxation without negative effects on LV contractility or pump function, and thus, there is a significant need for a new therapeutic approach for this particular type of heart disease.

Treatment of diastolic heart failure may be logically divided into three areas or categories: (1) removal of the precipitating cause, (2) correction of the underlying cause, and, (3) control of the congestive heart failure state. Treatment goals that have been advocated, by previously cited Mandinov, L. et al., and, by Braunwald, E., in "Heart Failure", Harrison's Principles of Internal Medicine, fourteenth edition, McGraw Hill publishers, are as follows:

1. Reduction of Central Blood Volume.

Reduction of salt intake and use of diuretics (usually, loop diuretics). Diuretics are effective in reducing pulmonary congestion, shifting the pressure-volume relation downwards. However, they must be used with care because the volume sensitivity of patients with diastolic dysfunction bears the risk that excessive diuresis may result in a sudden drop in stroke volume. Because of the steep pressure-volume relationship, a small decrease in diastolic volume will cause a large decrease of the filling pressure, and will result in a drop in stroke volume, and thus, in cardiac output.

2. Reduction of Workload.

Reduction of physical activity, maintenance of emotional rest and use of vasodilators. Vasodilators, such as sodium nitroprusside or ACE inhibitors reduce the filling pressure and the afterload in all patients, and elevate cardiac output. Reduction of an elevated left ventricular end diastolic pressure may improve subendocardial perfusion, thus improving myocardial contraction. Nonetheless, vasodilators have not been useful in the management of isolated diastolic heart failure and are more effective in combined heart failure, as indicated in the previously cited Braunwald, E. text. Vigorous control of hypertension is imperative in patients with heart failure caused by diastolic dysfunction, because control of hypertension may prevent progression or may partially reverse the disorder by addressing the primary cause of most cases, as described by Grauner, K., in "Heart Failure, Diastolic Dysfunction and the Role of the Family Physician", American Family Physician, 2001, 63: 1483-1486.

3. Improvement of LV Relaxation.

In particular, by using calcium channel blockers or ACE inhibitors. $Ca^{2+}$ channel blockers have been shown to improve myocardial relaxation and enhance diastolic filling. These drugs may be best matched to the pathophysiology of relaxation disturbances due to their ability to decrease cytoplasmic calcium concentration and reduce afterload. However, currently, use of $Ca^{2+}$ channel blockers is limited due to their negative inotropic effects (negative influence on the systolic function of the heart), and clinical trials have not clearly proven them to be beneficial.

4. Regression of LV Hypertrophy.

In particular, decrease in wall thickness and removal of excess collagen by ACE inhibitors and AT-2 antagonists or Spironolactone. Philbin, E. F., Rocco, T. A., Lindenmuth, N. W., Ulrich, K., and Jenkins, O. L., in "Systolic Versus Diastolic Heart Failure In Community Practice: Clinical Features, Outcomes, And The Use Of ACE Inhibitors", American Journal of Medicine, 2000, 109: 605-613, have shown that the use of ACE inhibitors in patients with ejection fraction equal to or greater than 0.50 was associated with a better NYHA class (New York Heart Association functional and therapeutic classification for stages of heart failure) after discharge from hospitalization, but had no significant effect on mortality or hospital readmission. ACE inhibitors and AT-2 antagonists affect blood pressure, reduce afterload, and affect the myocardium via the local renin-angiotensin system. These effects are important for regression of LV hypertrophy, and improvement of elastic properties of the myocardium.

5. Maintenance of Atrial Contraction and Control of Heart Rate.

In particular, by using beta-blockers and/or antiarrhythmics. Beta-blockers reduce blood pressure and myocardial hypertrophy. The positive effect on diastolic dysfunction is mainly due to slowing of the heart rate and not to a primary improvement in isovolumic relaxation or the diastolic properties of the left ventricle.

6. NO Donors.

NO (Nitric Oxide) donors have been shown to exert a relaxant effect on the myocardium, which is associated with a decrease in LV end diastolic pressure. In patients with severe LV hypertrophy, an increased susceptibility to NO donors has been documented, which may be beneficial for the prevention of diastolic dysfunction.

7. Heart Transplantation.

Heart transplantation is a definitive treatment for end stage heart failure.

8. Biventricular Pacing.

Biventricular pacing improves uncoordinated contraction due to left bundle branch block or other conduction abnormalities with wide 'QRS complex' (P-Q-R-S-T waveform) of an electrocardiogram, which are common in patients with CHF. Morris-Thurgood, J. A., Turner, M. S., Nightingale, A. K., Masani, N., Mumford, C., and, Frenneaux, M. P., in "Pacing In Heart Failure: Improved Ventricular Interaction In Diastole Rather Than Systolic Re-synchronization", Europace 2000, 2: 271-275, have shown that left ventricular pacing acutely benefits congestive heart failure patients with pulmonary capillary wedge pressure greater than 15 mm Hg, irrespective of left bundle branch block. They suggested the beneficial mechanism might be related to an improvement of ventricular interaction in diastole (VID) rather than ventricular systolic re-synchronization. According to their suggestion, LV pacing in patients with high LV end diastolic pressure, will delay right ventricular filling and allow greater LV filling before the onset of VID. Biventricular pacing, however, has not been clinically proven effective in the treatment of patients with diastolic heart failure.

To one of ordinary skill in the art, there is thus a need for, and it would be highly advantageous to have an in vivo device for use in improving diastolic function of the left ventricle of the heart, while minimally disturbing systolic function of the heart. Moreover, there is a need for such a device which is biocompatible and is specially configured for compact and long-term reliable use in humans.

One of the purposes of the present invention is to provide an indwelling in vivo device that may be used to improve diastolic function of either the left ventricle or right ventricle of the heart.

Another purpose of the present invention is to provide such a device that may be readily adapted to the precise topographic conformation of the heart that is to be treated.

Yet another purpose of the present invention is to provide such a device that may be readily delivered to the required site on the external surface of the ventricle by minimally-invasive means.

Yet another purpose of the present invention is to provide such a device that may be readily implanted on ventricles of different sizes and shapes, and that will be able to apply similar forces despite the dissimilarities.

Yet another purpose of the present invention is to provide such a device that may be readily implanted on the ventricle at different time points during the cardiac cycle and that will be able to apply similar outwardly-directed forces despite implantation at different time points.

Yet another purpose of the present invention is to provide such a device that will apply forces of an almost constant magnitude throughout the cardiac cycle.

Yet another purpose of the present invention is to provide such a device that will apply forces that act in a principally outward (Normal) direction.

Yet another purpose of the present invention is to provide a device that will absorb energy from cardiac motion along all axes of movement.

A further purpose of the present invention is to provide an in vivo device that overcomes the problems and disadvantages of previous devices.

Further objects and advantages of the present invention will become clear as the description proceeds.

SUMMARY OF THE INVENTION

The present invention relates to an in vivo device for improving diastolic function of the left or right ventricle of the heart, said device being a modification and improvement of the devices disclosed in co-pending international patent application no. PCT/IL02/000547 (published as WO 03/007778).

The modified device disclosed and described herein possesses certain advantageous features over and above those recited in the corresponding invention disclosed in the aforementioned international patent application, all of which advantages will be enumerated and described in more detail hereinbelow.

The present invention is primarily directed to an anatomically-compatible and physiologically-compatible in vivo device for improving diastolic function of either the left or right ventricle of the heart, comprising:

at least one elastic component in the form of a lattice capable of being arranged in a curved conformation such that one surface of said lattice may be adapted to the curvature of the external ventricular surface of the heart, or a portion thereof, wherein said at least one elastic component is capable of being operatively connected to the external ventricular surface of the heart by means of one or more connecting elements.

In order to achieve its desired clinical aim, the aforementioned elastic component needs to be capable of exerting a mainly radially outward expansive (i.e. normal) force on the external ventricular surface of the heart. The exertion of said expansive force by the device of the invention may be demonstrated and measured in vitro by means of using a force gauge (such as the Shimpo gauge) or a tension-compression machine (such as the Hounsfield H5K-S device, or any of the other similar devices known to the skilled artisan in the field.

Preferably, the aforementioned connecting elements may be attached to the lattice at attachment points located at the intersection of the horizontal and vertical members of said lattice. In a preferred embodiment, said attachment points are provided in the form of hollow attachment cups.

The lattice can be made of any biocompatible elastic material, such as silicone rubber, polyurethane or any other suitable biocompatible elastomer or biocompatible polymer. It can also be made of biocompatible metallic elements or a combination of both elastomer and metal. It can be produced via standard techniques as are well known in the art, in particular by means of injection molding or assembly of extruded elements or bending of metallic elements, or by combinations of these techniques.

The term "anatomically compatible" as used hereinbefore refers to the fact that the structure of the device of the invention is such that it may readily be adapted in situ to the precise shape and size of the heart to be treated.

The term "physiologically compatible" as used hereinbefore refers to the fact that the structure of the device of the invention is such that it may readily be adapted in situ to the precise movement vectors of the heart to be treated.

In one particularly preferred embodiment of the device of the invention, the elastic component comprises a lattice comprised of essentially quadrangular cells.

In another preferred embodiment of the device of the invention, the elastic component comprises a lattice comprised of essentially triangular cells. Many other geometrical configurations are also possible, all of which fall within the scope of the present invention.

In one particularly preferred embodiment of the invention, the elastic lattice is fitted with one or more preload elements. These elements are generally provided in the form of a ring, through which is fitted a rod, wire or pin. Both the ring and the rod, wire or pin may be constructed of a biocompatible metal or polymer. The purpose of said preload elements is to maintain one or more segments of the elastic lattice in a pre-bent ("preloaded") conformation, such that said segments are already loaded with stored elastic energy prior to implantation. By means of such preloading, the danger of causing undesirable compression or restriction of the ventricular wall is obviated, thus permitting the implantation of the elastic lattice onto the heart wall at any phase of the cardiac cycle.

In the present context, the term "longitudinal" as used herein in relation to the in vivo device of the invention refers to a plane that is approximately parallel with an imaginary line connecting the apex of the heart with the center point of its base. Also, the term "horizontal" is to be understood as referring to an essentially equatorial plane, that is, a plane that is approximately parallel with that defined in a transverse section of the heart. The term "lattice" used in connection with the elastic component of the present device indicates that said component comprises an array of approximately horizontal and vertical intersecting members, such that the intersection of said members creates a series of cells. Different lattices may therefore be constructed, each being characterized by the shape and size of the cells, the number of intersections (and hence cells) and the overall dimensions of the entire lattice.

Although the at least one elastic component of the in vivo device of the invention may be constructed of any suitable material possessing the desired spring-like properties, in a preferred embodiment, said at least one elastic component is constructed from a material selected from the group consisting of biocompatible silicone rubber, polyurethane or any other biocompatible elastomer. For example, injection of LSR silicone into a mold can be used, or alternatively, full profile silicone rods, or tubes, such as those filled with Elastosil E41 silicone adhesive, can be used.

According to one preferred embodiment of the device of the invention, said device is constructed such that the aforementioned value for the radially outward expansive pressure exerted on at least one part of the external ventricular wall is in the range of about 5 mm Hg to about 40 mm Hg.

Figures 4, 5B:
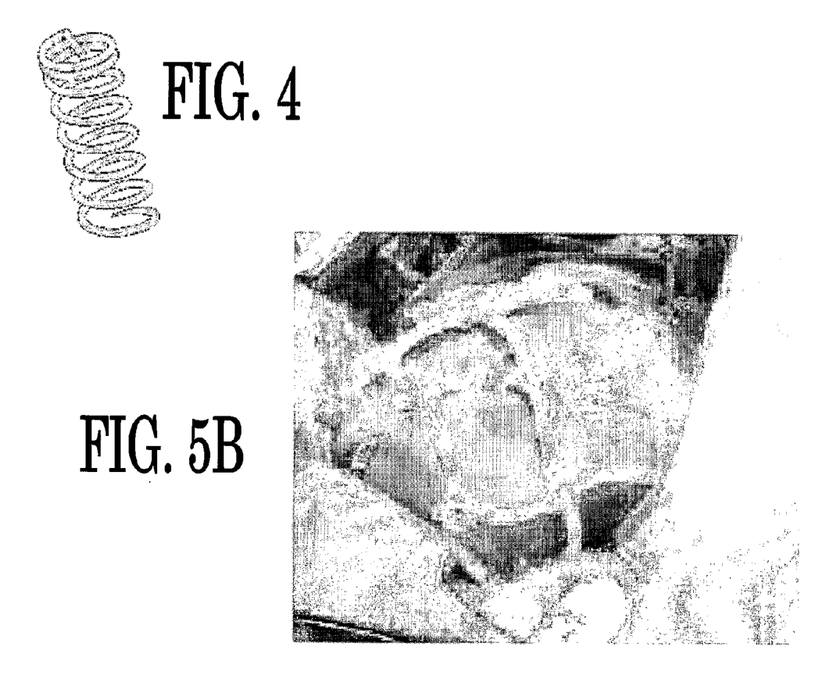
FIG. 4 illustrates the helical coil attachment mechanism.
FIG. 5B depicts the embodiment shown in FIG. 5A in its in situ position on the external cardiac wall.

The present invention is also directed to a connecting element suitable for connecting the medical device of this invention to the external ventricular wall of the heart, comprising helical coil springs (as shown in FIG. 4), which may be screwed into the cardiac tissue. The connecting elements can be made of any biocompatible material such as stainless steel, plastic, elastomer, degradable material etc. Other types of connecting elements can be used, such as (but not restricted to) biocompatible pins, biocompatible needles, biocompatible spikes, biocompatible screws, biocompatible clamps, biocompatible glue, biocompatible adhesion, surgical sutures, and, combinations thereof, having dimensions of length, height, and, width, depth, or thickness, each on the order of microns to centimeters, in the range of between about 10 microns to about 8 cm.

The device or part of the device can be coated by thin layers of film (for example a film comprising hydromers or parylene) for protection and friction reduction.

In another aspect, the present invention also encompasses a method for improving diastolic function of either the left or right ventricle of the heart, comprising attaching an anatomically-compatible and physiologically-compatible in vivo device as disclosed hereinabove to the external wall of said ventricle(s) by means of connecting elements, such that said device exerts a mainly radially outward expansive force, with minimal tangentially-directed forces on the external ventricular surface of the heart.

In one preferred embodiment of the method of the invention, the connecting elements are helical coil springs that may be screwed into the tissue of the external ventricular wall of the heart.

Preferably, the radially outward expansive pressure exerted on at least one part of the external ventricular wall is in the range of about 5 mm Hg to about 40 mm Hg.

As mentioned hereinabove, the in vivo device according to the present invention possesses a number of further significant advantageous properties in addition to those described in relation to the corresponding devices disclosed in co-pending international patent application no. PCT/IL02/000547 (published as WO 03/007778).

Among these advantages are included the following desirable properties:

a) Greater anatomical compatibility of the presently-disclosed device with the left ventricle of the heart to which said device is attached.
b) Greater physiological compatibility of the presently-disclosed device with the movement of the left ventricle of the heart to which said device is attached.
c) Increased range of forces and/or pressures attainable with a single device.
d) Increased range of left ventricular sizes that may be accommodated with a single device. Furthermore, the device may be readily implanted on ventricles of different sizes and shapes, and will be able to apply similar forces despite the dissimilarities in ventricular anatomy. In this regard, finite element analysis of the silicone segments (Nastran/Patran 2004) showed that the value of the force applied by the device on the heart can be controlled by the segment length, cross section diameter and material properties.
e) Increased ease with which the device may be delivered to the desired region of the left ventricle by minimally-invasive endoscopic means.
f) The device may be readily implanted on the ventricle at different time points during the cardiac cycle and will be able to apply similar outwardly-directed forces despite implantation at different time points. In this respect, finite element analysis of the device on a spherical surface, with different diameters between 100 mm and 40 mm, showed that the force at the mid junctions remains almost constant for diameters between 80 mm and 50 mm.
g) The device will apply forces of an almost constant magnitude throughout the cardiac cycle. Finite element analysis showed that the post buckling force developed at the end of the segments remains almost constant in the range of the applied loading.
h) The device will absorb energy from cardiac motion along all axes of movement.
i) The device will be radiolucent, and as such will not interfere during an angiography procedure, if such is required at any time after implantation of the device.
j) Significantly greater ease of construction of the device; and
k) Significantly lower cost of construction of the device.

Further properties and advantages of the presently-claimed device will become apparent as the description proceeds.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention.

FIG. 5 is a photographic representation depicting some examples of in vivo devices of the invention that incorporate an elastomeric lattice as their elastic element.

DESCRIPTION OF THE PREFERRED EMBODIMENTS

The present invention relates to an in vivo device for improving diastolic function of the left or right ventricle of the heart.

It is to be noted that the terms "ventricular", "ventricular surface", "ventricle" and the like are used herein to refer to either the left or right ventricles or to portions thereof. Thus, wherever the description refers to the left ventricle or portions thereof, it is to be appreciated that the teachings derived from said description apply equally to the right ventricle.

An advantage possessed by all embodiments of the presently claimed in vivo device is the fact that said device is capable of exerting externally-directed radial forces on the ventricular wall. These radially directed forces are of importance for the following two reasons:

1. they assist the diastolic movement of the left ventricle by allowing ventricular filling at lower filling pressures.
2. they minimize stress on cardiac myocytes, thus reducing oxygen consumption and preventing ischemia.

In order to further understand the latter point, it is necessary to further consider the physiological changes in ventricular shape and volume during the cardiac cycle. Thus the normal left ventricle performs a systolic wringing motion with clockwise rotation at the base (of approximately 4.4 degrees) and counterclockwise rotation at the apex (of approximately 6.8 degrees), as seen from the apex (Nagel E, Stuber M, Burkhard B, Fischer S E, Scheidegger M B, Boesiger P, Hess O M: "Cardiac rotation and relaxation in patients with aortic valve stenosis". European Heart Journal 2000; 21:582-589). This motion is analogues to the wringing of a wet towel to squeeze the water out; it allows the ventricle to generate high intraventricular pressures, with minimal shortening of the muscle fibers, and thus minimal energy expenditure. It is important to note that the rotation normally occurs during the isovolumic contraction phase, and there is no, or minimal rotation during systolic ejection.

During isovolumic relaxation an untwisting motion is observed, which is directed opposite to systolic rotation, counterclockwise at the base and clockwise at the apex. There is minimal rotation during the filling phase.

The elastomeric properties of the device presented herein allow myocardial twisting motion with minimal disturbance, due to the characteristics of the elastomer.

Referring now to FIG. 1, a main objective of treating a patient with diastolic dysfunction is to cause their abnormal diastolic pressure-volume relation curve (dashed line between 'c' and 'd') to go back to the diastolic pressure-volume relation curve of a normal subject, (dashed line between 'a' and 'b'), by decreasing the diastolic LV pressure for the same LV volume, during the entire diastolic stage of the cardiac cycle, in general, and, by decreasing the end diastolic LV pressure for the same LV volume (indicated by the arrow), in particular. The present invention accomplishes this.

The device of the present invention is based on applying a outward expansive force or pressure (force per unit area) to the wall region of the left ventricle, in order to reduce intraluminal hydrostatic pressure of the left ventricle, also known as LV filling pressure, during the ventricular diastolic stage of the cardiac cycle, thereby, improving diastolic function of the left ventricle of the heart, while minimally disturbing systolic function of the heart.

Reduction of hydrostatic pressure within the left ventricle has the beneficial effect of reducing hydrostatic pressure in other cardiac compartments and organs preceding, that is, upstream relative to, the left ventricle in the overall cardiac system, in particular, in the left atrium, and in the pulmonary vasculature of the venous system supplying blood to the atrium. These beneficial effects prevent both dilatation of the atria with propagation to atrial fibrillation, and pulmonary congestion causing symptoms of dyspnea and pulmonary edema.

Normal left ventricular end diastolic pressure (LVEDP) is in the range of about 6-12 mm Hg, and the upper end of this range can increase to above 35 mm Hg during conditions of heart failure involving diastolic dysfunction, as a direct result of the left ventricle needing relatively high hydrostatic filling pressures in order to achieve the necessary left ventricular end diastolic volume (LVEDV) for an appropriate cardiac output. Accordingly, an important objective of the present invention is to significantly reduce the hydrostatic pressure in the left ventricle during the diastolic stage of the cardiac cycle, thereby, improving diastolic function of the left ventricle of the heart, while minimally disturbing systolic function of the heart. In particular, fulfilling this objective includes sufficiently reducing left ventricular end diastolic pressure (LVEDP), preferably, down to the normal range of about 6-12 mm Hg, during ventricular diastole of the heart.

In addition to the primary use of the present invention in treating subjects having symptoms of diastolic heart failure, by reducing intraluminal hydrostatic pressure (LV filling pressure) of the left ventricle during the ventricular diastolic stage of the cardiac cycle, thereby, improving diastolic function of the left ventricle of the heart, while minimally disturbing systolic function of the heart, the present invention can be used in a variety of other cardiac related and/or non-related monitoring applications, such as pressure measurement applications, and, therapeutic applications, such as in drug delivery applications. For example, the device of the present invention can be used together with an apparatus for time controlled drug delivery or release to the body, in general, and, to the cardiac region, in particular.

It is to be understood that the phraseology and terminology employed herein are for the purpose of description and should not be regarded as limiting. For example, in describing the present invention, the key functionality terms 'elasticity' and 'resiliency', and, the corresponding variant terms 'elastic' and 'resilient', are considered synonyms, and for the purpose of brevity, while maintaining clarity of description, the terms 'elasticity' and 'elastic', are solely used hereinafter, however, it is to be fully understood that the corresponding synonymous terms 'resiliency' and 'resilient', respectively, are equally applicable.

The component parts, operation, and implementation of an anatomically compatible and physiologically compatible in vivo device for improving diastolic function of the left ventricle of the heart according to the present invention are better understood with, reference to the following description and accompanying drawings. Throughout the following description and accompanying drawings, like reference numbers refer to like elements.

The device of the present invention utilizes the physicochemical property and behavior of elasticity or resiliency, in a relatively simple manner, in appropriately constructed and configured elastic or resilient components of the device operatively connected to the external surface of a wall region of the left ventricle, for exerting an elastic or resilient type of the expansive force or pressure to the wall region of the left ventricle, for reducing intracardiac pressure during ventricular diastole of the heart, thereby, improving diastolic function of the left ventricle of the heart, while minimally disturbing systolic function of the heart.

The ventricular device of the present invention may be constructed from either a single type of material, or, from a plurality of different types of materials. Preferably, the ventricular device is constructed from a biocompatible elastic material, such as silicone rubber, polyurethane or any other suitable biocompatible elastomer or biocompatible polymer. In a particularly preferred embodiment, the device is constructed by means of placing rods of the desired polymeric material (e.g. silicone rubber) in a mold, in accordance with the required dimensions and form (i.e. in accordance with the different segment length requirements), and cut to size at the beginning of the first junction. At every junction, a molded silicone cup is inserted and attached to the rod by means of a polymeric adhesive (for example, Elastosil E41). The above steps are repeated until the complete lattice of the desired size is created.

The device may also be made of biocompatible metallic elements or a combination of both elastomer and metal. It can be produced via injection molding or assembly of extruded elements or bending of metallic elements, or both techniques. For example, such metals are selected from the group consisting of a pure metal, a metal alloy, and, combinations thereof. Exemplary pure metals are tungsten, platinum, and, titanium. Exemplary metal alloys are nitinol, and, stainless steel.

The ventricular device of the present invention, in general, and, the at least one elastic component, in particular, have dimensions of length, height, and, width, depth, or thickness, each on the order of microns to centimeters, in the range of between about 10 microns to about 8 cm.

The geometry, shape, form, and, dimensions, and, elastic strength, of the ventricular device, in general, and, the at least one elastic component, in particular, are specifically determined, in part, according to the desired or necessary extent or degree of elasticity, for properly and optimally performing the critical function of potentially exerting radially outward forces or pressures (in a range of about 5-40 mm Hg, preferably, about 10 mm Hg) to the outer wall surface of the left ventricle, in order to properly fulfill the main objective of sufficiently reducing intracardiac hydrostatic pressure during ventricular diastole of the heart, thereby, improving diastolic function of the left ventricle of the heart, while minimally disturbing systolic function of the heart. This includes sufficiently reducing left ventricular end diastolic pressure (LVEDP), preferably, down to the normal range of about 6-12 mm Hg, during ventricular diastole of the heart.

Following are description and accompanying drawings for describing and illustrating, respectively, various embodiments of the device of the present invention.

Figure 2:
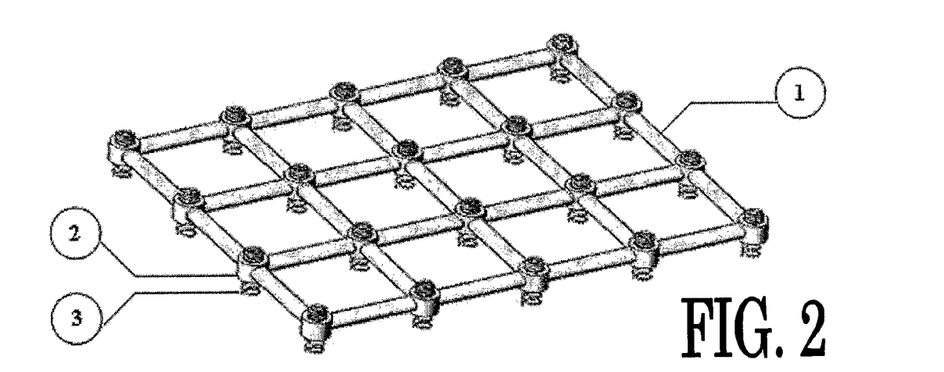
FIG. 2 depicts a preferred embodiment of the in vivo device of the invention, in which said device comprises a lattice or net formation

Referring again to the drawings, FIG. 2 depicts one preferred embodiment of the device of the present invention, generally indicated by numeral 1, comprising an elastic lattice which is attached to the heart surface through multiple attachment points. Each attachment point consists of attachment cup (2) and attachment spring (3). For illustration purposes the lattice is constructed of quadrangular cells, however it may be constructed of other variable designs.

In one embodiment of this device, each attachment cup (2) can have a biocompatible fabric or mesh attached to the side which will be connected to the ventricular wall. Such fabric will increase the local fibrotic tissue reaction to the connecting element, and this may have a benefit of increasing the adherence of the device to the myocardium. Exemplary materials suitable for this include Dacron and polytetrafluoroethylene (PTFE). Dacron originally intended for use as arterial grafts is highly suitable for this purpose, and may be commercially obtained from C. R. Bard, Inc., Murray Hill, N.J., USA.

Exemplary dimensions of the embodiments of the device depicted in FIG. 2 are as follows: Longitudinal and horizontal length of each segment (that is, the length of each arm of the quadrangular cell) is in the range of 5-50 mm, preferably about 20 mm, the longitudinal and horizontal lengths of the whole device, (that is, the length extending along imaginary central longitudinal axis of the device) are in the range of between about 1 cm to about 10.0 cm, preferably, about 6 cm. The average depth or thickness of the elastomeric rod of the device is in the range of between about 0.5 mm to about 5.0 mm preferably, about 3 mm.

It is to be noted that the above measurements are given as illustrative examples of the dimensions of a typical device of the invention. In practice, however, the dimensions and the design of the lattice—including the shape and dimensions of the elastic elements cross section, the length of the elastic elements, the physical characteristic of the elastic material, and so on—can all be changed in accordance with clinical requirements and manufacturing practices and standards.

Figure 3:
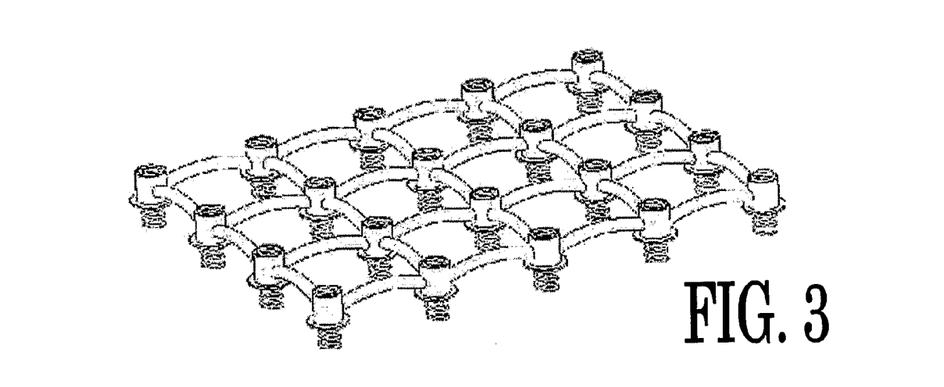
FIG. 3 is an illustration of the device depicted in FIG. 2 shown in its preloaded state.

FIG. 3 depicts an embodiment of the device described hereinabove in a preloaded state. To optimize the functionality of the device, it can be loaded with elastic energy before attachment to the surface of the heart. The pre-load can be achieved by bending the elastic elements with clamps, and holding the device in its pre-load state. After attaching the device to the heart the clamps are easily removed, thus allowing full functionality of the device. Using a preload mechanism has the advantage of allowing the device to exert radially outward forces throughout the cardiac cycle, and prevents the possibility of restriction of the heart by the device.

In a further embodiment, preload is achieved by the use of preload pins incorporated into the silicon lattice, as will be described in further detail hereinbelow.

FIG. 4 illustrates an example of the above-described attachment mechanism, the helical coil spring, which may be screwed into the cardiac tissue in a corkscrew like manner.

The helical coil attachment mechanism may be constructed of any suitable elastic material. An exemplary material is metal wires or tubes. Examples of metals possessing the required physical properties include (but are not limited to) stainless steel 316 and NITINOL (Nickel Titanium), both of which are biocompatible metals that are commercially available in the form of wires or tubes. For examples, wires of both materials may be obtained from Allvac Inc., Monroe, N.C. In the case of wires, industrial bending machinery may be used to bend the wire into the desired shape. Additional exemplary materials for constructing the helical coil attachment mechanism are biocompatible polymers. The advantage of these materials is that they are radiolucent, and as such will not interfere during an angiography procedure, if such is required at any time after implantation of the device of this invention.

Figure 5A:
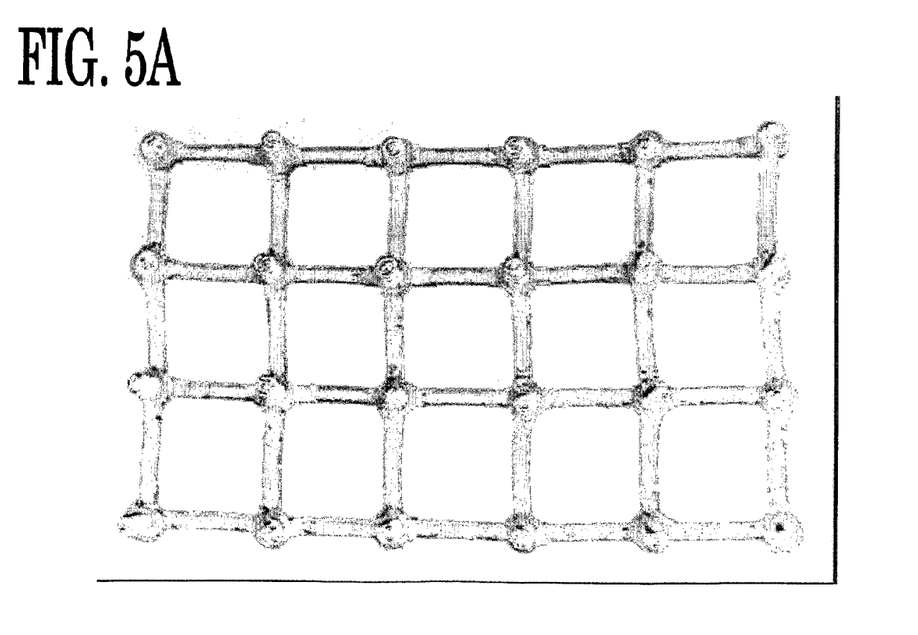
FIG. 5A shows a device comprising a silicon lattice.

FIG. 5 is a photographic representation depicting some exemplary devices of the invention that incorporate an elastomeric lattice as their elastic element. FIG. 5A shows a device comprising a silicon lattice. The device is shown in its resting state, and the helical coil attachment mechanisms are shown in the attachment cups. FIG. 5B depicts the embodiment shown in FIG. 5A in its in situ position on the external wall of the left ventricle. This photo was taken during an in-vivo study of the device on a sheep heart. The device was connected to the left ventricle by using the helical coil attachment. Connecting the device was a simple procedure, taking approximately 5 minutes, and was performed on a beating heart, without the use of cardiopulmonary bypass.

Figure 6:
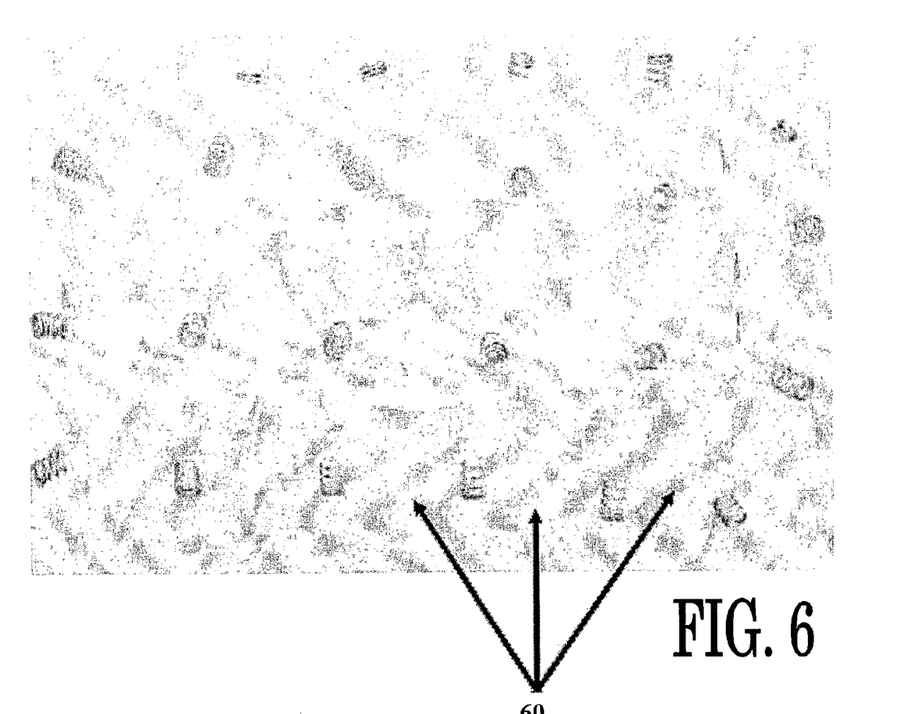
FIG. 6 is a photographic representation of a device comprising a silicon lattice with preload pins, to ensure device preloading before implantation to the ventricular wall.

FIG. 6 is a photographic representation of a device comprising a silicon lattice with preload pins (indicated by numeral 60). The preload pins ensure preloading of the device before implantation to the ventricular wall, and prevent the occurrence of constriction of the ventricular wall. By means of these preload pins, each segment of the device is preloaded with initial energy, thereby permitting the device to be implanted at any stage of the cardiac cycle without the risk of constriction of the ventricular wall (i.e. the very opposite of the desired therapeutic effect). In general, preloading may be achieved, for example, by bending each segment (prior to implantation onto the heart wall) and then maintaining each said segment in the bent (i.e. preloaded) state by various means such as small silicone rings fitted with appropriately-sized plastic pins, or alternatively, metal rings used together with metal wire. In a preferred embodiment of the device of the invention, the preload elements are 25 mm long rods of silicone having a linear elastic modulus (E) of 3 MPa. Preloading may be achieved for every segment separately (i.e. one preload element for each segment) or across multiple segments by means of the use of either multiple preload elements or a single, large such element. After attachment of the device to the heart, the preload elements (e.g. preload pins) are removed, following which the segments of the lattice remain loaded with the initial preload energy.

Figure 7:
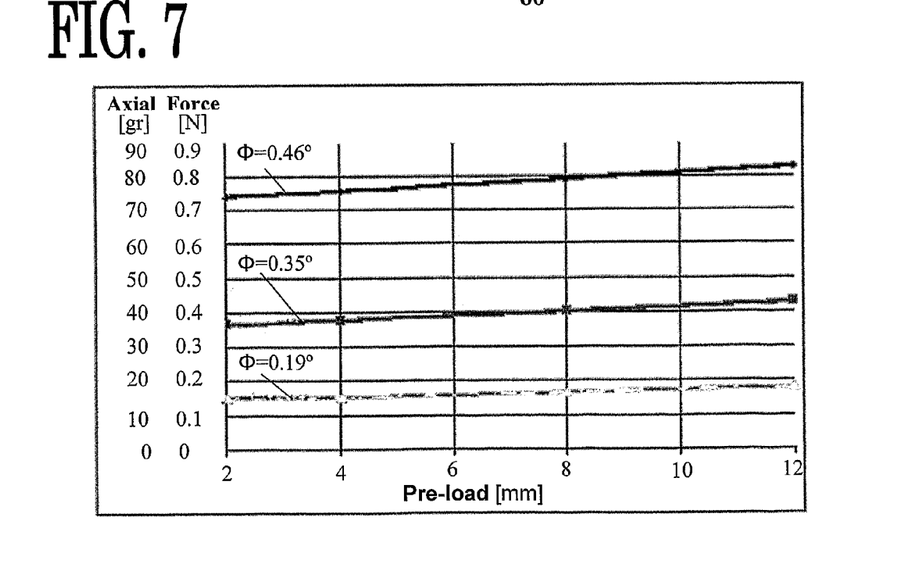
FIG. 7 is a graph representing the axial forces developed by a segment of the device of the invention Vs. the preloading of the device.

FIG. 7 is a graph representing the axial forces developed by a segment of the device of the invention versus the preloading of the device. (Calculations were performed using finite element analysis software.) Preloading is shown in millimeters and represents the length of shortening of the segment from its original, expanded (resting) state. Calculations are shown for three representative diameters of 25 mm long silicone preload pins, having a linear elastic modulus (E) of 3 MPa (2 mm—lower line, 2.5 mm—middle line, and 3 mm—upper line). The calculation demonstrates three of the significant advantages of the device of the invention, in which the device will apply forces of an almost constant magnitude throughout the cardiac cycle, even when connected to the ventricle at different time points of the cardiac cycle, and even when implanted on hearts of differing size and shape. The angular values given above each line on the graph represent the slope of that line. The small angle values obtained indicates that the relationship between the preloading of the segments and the applied force is almost constant. The clinical significance of this fact is that the applied force will be almost constant through the cardiac cycle (i.e. the force loaded onto each segment of the device during systole will be released during diastole).

Figure 8:
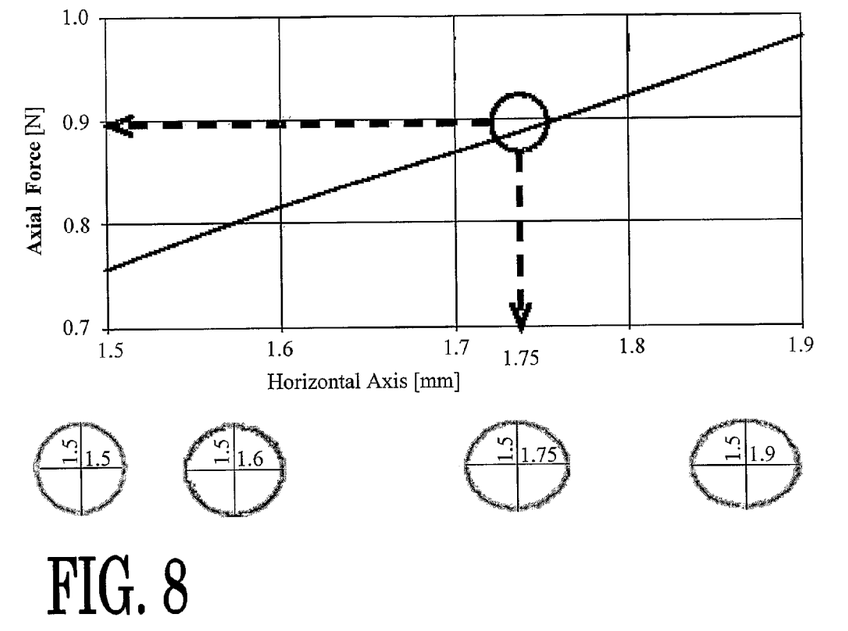
FIG. 8 is a graph representing the axial forces developed by a segment of the device of the invention Vs. the horizontal axis of the cross-section of the segment.

FIG. 8 is a graph representing the axial forces developed by a segment of the device of the invention Vs. the horizontal axis of the cross-section of the segment. The purpose of this analysis was to evaluate an elliptical cross section Vs. a round cross section. It is shown that an elliptical cross section has the benefits of increasing the outwardly-directed radial force of the device. Similar benefits may be obtained by using a triangular cross-section, or many other cross section designs aimed at controlling the direction of the forces. Preloading in this calculation represents the percentage of shortening of the segment from its original, expanded (resting) state (16%). The calculation demonstrates another significant advantage of the device of the invention, in which the device will apply forces that are principally in an outward (Normal) direction, with minimal tangentially directed forces, thus reducing myocardial stress, and minimizing the disturbance of myocardial twisting motion. Calculations were performed using finite element analysis software using model silicone pins of length 25 mm having an elastic modulus of 3 MPa.

Figure 9:
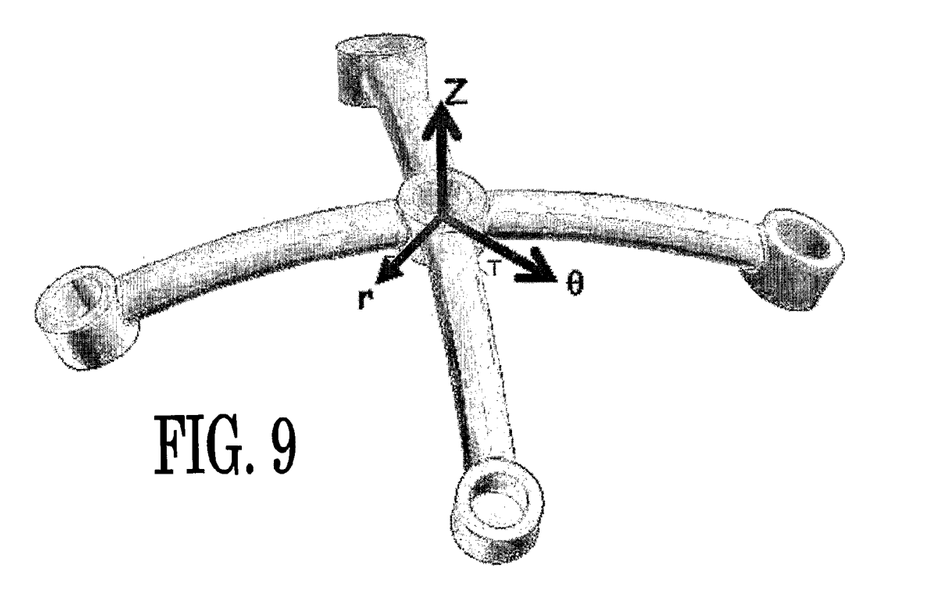
FIG. 9 illustrates the forces applied by an element of the device shown previously in FIGS. 2 and 3. The arrows represent force vectors applied by the device to the area of the heart to which it is attached.

FIG. 9 illustrates the forces applied by an element of the device shown previously in FIGS. 2 and 3. The arrows represent force vectors applied by the device to the area of the heart to which it is attached (the attachment cups are shown, and the helical coil attachment mechanism is not shown). Z represents a radially outward direction (Normal forces), while θ and r represent tangential forces.

The following table provides an example of the forces developed at the mid-junction of the device of the invention (as shown in FIG. 9) during contraction of the heart. The purpose of this analysis was to evaluate the forces applied by the device on the ventricular surface. It is shown that within a wide range of diameters the Normal forces are constant, and that the normal forces are significantly larger then the tangential forces. The calculation demonstrates two significant advantages of the device of the invention: 1—As shown in the table, the device will apply forces that are principally in an outward (Normal, shown as Z direction in FIGS. 9 and 10) direction, with minimal tangentially directed forces (shown as θ and r directions in FIG. 9), thus reducing myocardial stress, and minimizing the disturbance of myocardial twisting motion. 2—As shown in the table, the device will apply forces that are almost constant within a wide range of diameters. The calculations were performed using finite element analysis software.

The forces developed at the mid. junction:

| Heart Diameter [mm] | Θ (tangent forces) | r | Z (Normal Force) |
|---|---|---|---|
| 100 | 0 | 0 | 0 |
| 98 | 0.04 | 0.14 | 27.50 |
| 96 | 0.08 | 0.32 | 47.55 |
| 94 | 0.13 | 0.47 | 61.40 |
| 92 | 0.24 | 0.70 | 71.14 |
| 90 | 0.21 | 0.75 | 78.22 |

-continued

The forces developed at the mid. junction:

| Heart Diameter [mm] | Θ (tangent forces) | r | Z (Normal Force) |
|---|---|---|---|
| 88 | 0.39 | 0.77 | 84.65 |
| 85 | 0.34 | 0.99 | 90.58 |
| 80 | 0.52 | 1.52 | 99 |
| 75 | 0.72 | 1.45 | 107.45 |
| 70 | 0.11 | 2.01 | 100.59 |
| 60 | 1.08 | 0.56 | 95.28 |
| 50 | 3.53 | 5.91 | 92.93 |
| 40 | 18.36 | 27.50 | 16.06 |

Figure 10:
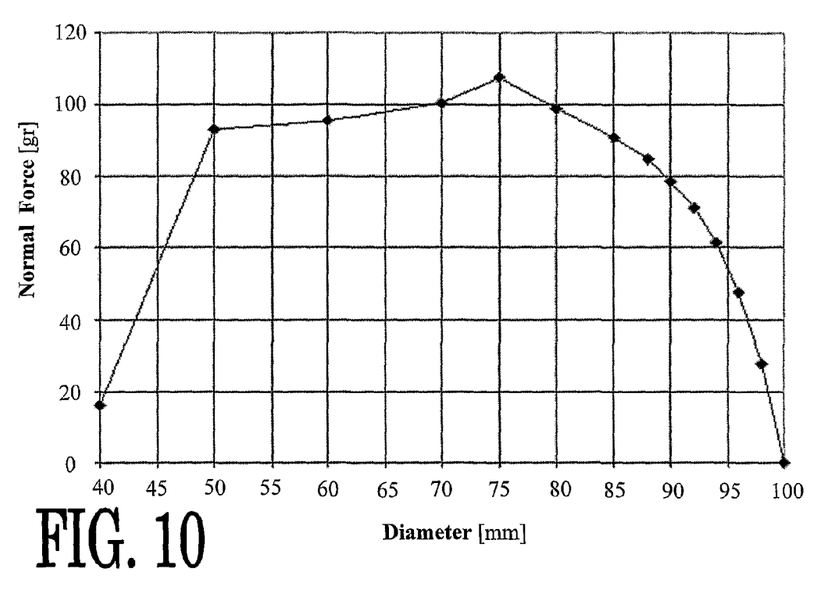
FIG. 10 is a graph representing the radially outward (Normal) forces developed by a segment of the device of the invention during different heart (and device) diameters.

FIG. 10 is a graph representing the radial outward (Normal, shown as Z direction in FIG. 9) forces developed by a segment of the device of the invention during different heart (and device) diameters. It is important to note that the average diameters of the left ventricle, as measured with echocardiography, are approximately 55 mm in end systole and 65 mm in end diastole. In view of this, it may be recognized from the graph that the outward (normal) forces applied by the device are approximately constant within these ranges of cardiac diameters. The calculation demonstrates a significant advantage of the device of the invention, in which the device will apply forces that are almost constant within a wide range of diameters. Calculations were performed using infinite element analysis software.

The embodiments of the device of the invention described hereinabove and depicted in FIGS. 2 and 3 may be inserted in place using a minimally invasive surgical procedure, such as a thoracoscopy, or, thoracotomy, with a relatively small diameter delivery system for delivering and deploying the ventricular device into the body, in general, and to a left ventricular cardiac outer wall surface, in particular.

Constructing the device from an elastomeric material, or a biocompatible polymer, facilitates the use of minimally invasive insertion procedures such as those described above, since it allows the device to easily fold into a very small size, without loosing any of its elastic properties. Thus, the device may be inserted into the body cavity through a very small aperture, using a minimally invasive procedure. Techniques and equipment of thoracoscopy deployment are well taught about in the prior art.

The following non-limiting working example illustrates the insertion and use of the in vivo device of the present invention in a healthy mammalian subject.

Example

In Vivo Demonstration of the Implantation and Use of the Device of the Present Invention in a Mammalian Subject Methods Note: All animals in the study received humane care in compliance with the Public Health Service Policy on Humane Care and Use of Laboratory Animals, prepared by the office of laboratory animal welfare—National Institute of Health, amended August 2002.

Anesthesia and Instrumentation:

A healthy sheep, (12 month, 40 Kg) was anesthetized as follows:
1. Induction: I. M Ketamine 5 mg/kg & Xlyazine 0.25 mg/kg.
2. Intubation and artificial ventilation.
3. Maintenance of anesthesia by Isoflurane (0.5%-2.5%)

4. Following intra-tracheal intubation, positive pressure mechanical ventilation was instituted using the above inhalants.
5. A peripheral vein was cannulated for crystalloid solution infusion to assist the maintenance of stable hemodynamics.

Test Procedure:

The following test procedure was then performed:
1. Left thoracotomy and pericardiotomy were performed.
2. ECG electrodes were connected and monitored.
3. The heart was paced by an external pacemaker to 80 bpm.
4. A Mikro-Tip pressure intravascular catheter (Millar, Houston, Tex.) was introduced into the left ventricle via the left atrium. The catheter was immersed in 0.9% NaCl solution prior to use. Prior to introduction, the transducers were calibrated using a control unit with a calibration circuit to provide an electrical zero, 20 mmHg and 100 mmHg calibration signals. The system provides accurate high fidelity pressure monitoring with no damping or danger of air embolism. The pressure signals were amplified using a Millar amplifier with a flat frequency response up to 2 KHz. 180 seconds, comprising a single data run of LV pressures were sampled digitally at 200 Hz using an A/D multifunctional data acquisition card (PowerLab Inc.). Data was transferred to a personal computer for storage, using a PowerLab custom acquisition program developed in the LabView environment (National Instruments, Austin, Tex.). The signals were later processed and analyzed using MATLAB 6.5.
5. Baseline data acquisition runs were initiated after allowing sufficient time for hemodynamic stabilization before starting the study. Hemodynamic stabilization time before
6. Attachment of the device is detailed in the device attachment section.
7. Recording duration for each trace sample was 3 minutes.
8. The pericardium was sutured using multiple stitches of 4/0 prolene. The chest was sutured closed.
9. Anesthetic protocol was stopped, and the animal was awakened.

Device Attachment and Testing:

The device was placed on the external surface of the left ventricle and connected using the helical coil attachment mechanism. The device was located between the LAD coronary artery and the PDA coronary artery (on its LV aspect). The basal end of the device was set approximately 1 cm from the AV groove, whereas the apical end was set approximately 3 cm from the Apex. The preload pins were released after the attachment of each segment of the device.

7 segments of the device were attached, with 14 spiral attachment mechanisms, as shown in FIG. 5B.

Left ventricular pressures were measured in the following sequence:
1. Baseline.
2. After attachment of every device segment and release of the preload pins.
3. Before chest closure, after removal of surgical retractors.

Results:

During the experiment the sheep maintained a stable hemodynamic state.

Figure 11:
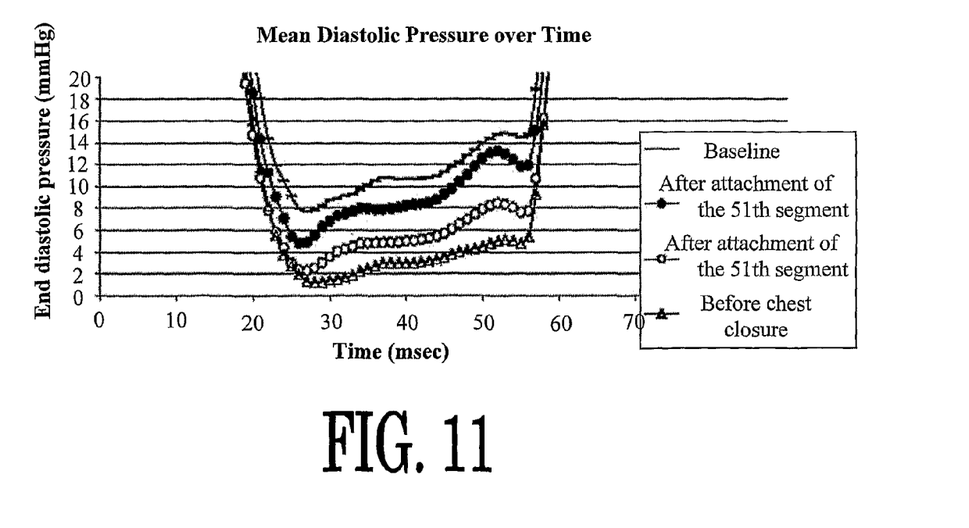
FIG. 11 is a graph representing the Left Ventricular diastolic pressures measured during an in-vivo study of an exemplary device of the invention. Every curve is a mean of over 180 cardiac cycles.

The attachment procedure was technically simple and quick, taking less than 1 minute for each device segment. No negative side effects were encountered during the attachment procedure. The mean pressure-over time curves, measured during the procedure are presented in FIG. 11. Four representative measurements are shown in FIG. 11:
1. Baseline.
2. After 5 segments were attached.
3. After 7 segments were attached.
4. Before chest closure, after removal of surgical retractors.

In the graph presented in FIG. 11 every curve is a mean of over 180 cardiac cycles. The pressure curves demonstrate a dose response to the increasing left ventricular surface coverage. With high surface coverage of the device, LV diastolic pressures were reduced by approximately 10 mmHg compared to baseline. Cardiac motion was not impaired by observation. Furthermore, the dynamic properties of the elastic lattice device were in good correlation with the twisting motion of the heart.

The invention claimed is:

1. An anatomically-compatible and physiologically-compatible in vivo device for improving diastolic function of either the left or right ventricle of the heart, comprising:
  at least one unified elastic component in the form of a lattice, said lattice in the form of an array of approximately straight horizontal and vertical intersecting members such that the intersection of said members creates a series of cells, wherein each cell is bounded by said straight intersecting members,
  and wherein said approximately straight members are continuous from one edge of said lattice to the other,
  said lattice capable of being arranged in a curved conformation such that one surface of said lattice may be adapted to the curvature of the external ventricular surface of the heart, or a portion thereof, and is capable of exerting a mainly radially outward expansive force on the external ventricular surface of the heart,
  wherein said at least one elastic component is capable of being operatively connected to the external ventricular surface of the heart with one or more connecting elements operatively connecting the at least one elastic component to the external ventricle surface of the heart,
  wherein said device makes provision for the attachment of said one or more connecting elements to the elastic lattice at attachment points located at the intersection of said horizontal and vertical intersecting members of said lattice:
  wherein said connecting elements are adapted to be attached to the external ventricular wall of the heart and embedded therein and comprised from one or more elements from a group consisting of:
    a) helical coil springs adapted to be screwed into the cardiac tissue,
    b) biocompatible pins,
    c) biocompatible needles,
    d) biocompatible spikes, and
    e) biocompatible screws.
2. The anatomically-compatible and physiologically-compatible in vivo device according to claim 1, wherein the lattice comprises essentially quadrangular cells.
3. The anatomically-compatible and physiologically-compatible in vivo device according to claim 1, wherein the lattice comprises essentially triangular cells.
4. The anatomically-compatible and physiologically-compatible in vivo device according to claim 1, wherein the elastic lattice is made of one or more biocompatible polymers.
5. The anatomically-compatible and physiologically-compatible in vivo device according to claim 1, wherein the polymer is a biocompatible elastomer.
6. The anatomically-compatible and physiologically-compatible in vivo device according to claim 5, wherein the elastomer is silicone rubber.
7. The anatomically-compatible and physiologically-compatible in vivo device according to claim 5, wherein the elastomer is polyurethane.

8. The anatomically-compatible and physiologically-compatible in vivo device according to claim 1, wherein the elastic lattice is made of at least one elastomer and at least one biocompatible metal.

9. The anatomically-compatible and physiologically-compatible in vivo device according to claim 1, wherein the lattice is fitted with a plurality of preload elements, said elements being capable of applying a preload force to said lattice.

10. The anatomically-compatible and physiologically-compatible in vivo device according to claim 1, wherein the at least one elastic component is capable of exerting radially outward expansive force on the external ventricular surface of the heart in the range of about 5 mm Hg to about 40 mm Hg.

11. The anatomically-compatible and physiologically-compatible in vivo device according to claim 1, wherein said device, or a part thereof, is coated by a thin layer of a protective film, wherein said film is comprised of a material selected from the group consisting of hydromers and parylene.

12. A method for improving diastolic function of either the left or right ventricle of the heart, comprising attaching an anatomically-compatible and physiologically-compatible in vivo device according to claim 1 to the external wall of said ventricle(s), by means of connecting elements, such that said device exerts a mainly radially outward expansive force on the external ventricular surface of the heart.

13. The method according to claim 12, wherein the connecting elements are helical coil springs that may be screwed into the tissue of the external ventricular wall of the heart.

14. The method according to claim 12, wherein the radially outward expansive pressure exerted on at least one part of the external ventricular wall is in the range of about 5 mm Hg to about 40 mm Hg.

* * * * *